(12) United States Patent (10) Patent No.: US 6,684,880 B2
Trueba (45) Date of Patent: Feb. 3, 2004

(54) APPLICATOR FOR DISPENSING BIOACTIVE COMPOSITIONS AND METHODS FOR USING THE SAME

(75) Inventor: Kenneth E. Trueba, Philomath, OR (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 0 days.

(21) Appl. No.: 10/007,133

(22) Filed: Dec. 4, 2001

(65) Prior Publication Data

US 2003/0101991 A1 Jun. 5, 2003

(51) Int. Cl.[7] .......................... A61M 11/00; B05B 17/06
(52) U.S. Cl. ............................. 128/200.16; 128/200.19; 128/203.15; 128/203.12
(58) Field of Search ................. 261/154, 130, 261/104, 107, DIG. 65; 128/203.13, 203.15, 203.17, 203.26, 203.27, 203.28, 200.16, 200.14; 604/58

(56) References Cited

U.S. PATENT DOCUMENTS

| 5,002,048 | A | * | 3/1991 | Makiej, Jr. ............. 128/200.23 |
| 5,169,029 | A | * | 12/1992 | Behar et al. ..................... 222/1 |
| 5,284,133 | A | * | 2/1994 | Burns et al. ........... 128/200.23 |
| 5,437,267 | A | * | 8/1995 | Weinstein et al. ..... 128/200.23 |
| 5,520,166 | A | * | 5/1996 | Ritson et al. .......... 128/200.14 |
| 5,664,557 | A | * | 9/1997 | Makiej, Jr. ............. 128/200.23 |
| 5,881,716 | A | | 3/1999 | Wirch et al. |
| 5,894,841 | A | * | 4/1999 | Voges .................... 128/203.12 |
| 6,014,970 | A | * | 1/2000 | Ivri et al. .............. 128/200.16 |
| 6,116,516 | A | * | 9/2000 | Ganan-Calvo ................ 239/8 |
| 6,158,431 | A | * | 12/2000 | Poole .................... 128/203.12 |
| 6,165,155 | A | | 12/2000 | Jacobsen et al. |
| 6,190,326 | B1 | * | 2/2001 | McKinnon et al. ......... 600/529 |
| 6,196,218 | B1 | * | 3/2001 | Voges .................... 128/200.14 |
| 6,202,642 | B1 | * | 3/2001 | McKinnon et al. .... 128/200.23 |
| 6,234,167 | B1 | * | 5/2001 | Cox et al. ............. 128/200.14 |
| 6,325,062 | B1 | * | 12/2001 | Sosiak ................... 128/203.25 |
| 6,325,475 | B1 | * | 12/2001 | Hayes et al. ................... 347/2 |
| 6,358,058 | B1 | * | 3/2002 | Strupat et al. .............. 434/262 |
| 6,390,453 | B1 | * | 5/2002 | Frederickson et al. ........ 261/26 |
| 6,435,175 | B1 | * | 8/2002 | Stenzler ................. 128/200.14 |
| 6,523,536 | B2 | * | 2/2003 | Fugelsang et al. ..... 128/200.14 |
| 6,543,443 | B1 | * | 4/2003 | Klimowicz et al. .... 128/200.23 |

* cited by examiner

Primary Examiner—Weilun Lo
Assistant Examiner—Michael G Mendoza (57) ABSTRACT

An applicator for delivering a bioactive composition includes a jet dispenser having an orifice for ejection of droplets from the dispenser. The jet dispenser further includes a main body. At least partially insertable through the main body is a replaceable fluid reservoir for holding and delivering the bioactive composition to the orifice for ejection therethrough. A body orifice spacer is positioned between the orifice of the dispenser and a target during ejection of the bioactive composition to the target.

30 Claims, 2 Drawing Sheets

FIG.3

APPLICATOR FOR DISPENSING BIOACTIVE COMPOSITIONS AND METHODS FOR USING THE SAME

FIELD

This invention relates to administration of compositions (such as pharmaceutical compositions), including compositions administered topically or delivered to a mucous membrane, such as via inhalation. In particular, this invention combines the unrelated technologies of pharmaceutical administration and inkjet technology.

BACKGROUND

Bioactive compositions, such as pharmaceuticals, provide effective treatments for a variety of illnesses. Unfortunately, administration of therapeutically effective doses of many medications can be difficult in some instances. For example, some drugs (particularly peptide based drugs, such as insulin) are partially or totally inactivated by the highly acidic environment of the stomach if orally ingested. Another problem is the "first pass" effect, which refers to the partial inactivation of orally ingested drugs in the liver after they have been absorbed from the gastrointestinal system and before they have exerted their full therapeutic effect. In addition to such physiological obstacles to administration, patients often fail to take their medications at the proper prescribed intervals or for the necessary period of time.

In addition to oral ingestion, inhalational administration has been used as an alternative route of drug delivery. Inhaled drugs can be absorbed directly through the mucous membranes and epithelium of the respiratory tract, thereby minimizing initial inactivation of bioactive substances by the liver. Inhalational delivery also can provide drugs directly to therapeutic sites of action (such as the lungs or the sinuses). This mode of administration has been particularly effective for the delivery of pulmonary drugs (such as asthma medications) and peptide based drugs (usually via intranasal administration), using metered dose inhalers (MDIs). However, MDIs often require coordinating inhalation with actuation of the MDI, and some patients are not able to master this technique. Moreover, patients often forget to take medications at prescribed times or with the prescribed frequency, and some patients inadvertently or inappropriately use medications, leading to hospitalizations, permanent injury, and even death.

SUMMARY

An applicator for delivering a bioactive composition includes a jet dispenser having an orifice for ejection of droplets from the dispenser. The jet dispenser further includes a main body. At least partially insertable through the main body is a replaceable fluid reservoir for holding and delivering the bioactive composition to the orifice for ejection therethrough. A body orifice spacer is positioned between the orifice of the dispenser and a target during ejection of the bioactive composition to the target.

DETAILED DESCRIPTION

Unless otherwise noted, technical terms are used according to conventional usage. Definitions of common terms in pharmacology may be found in *Remington: The Science and Practice of Pharmacy*, $19^{th}$ Edition, published by Mack Publishing Company, 1995 (ISBN 0-912734-04-3); different routes of delivery to mucous membrances is discussed in particular at pages 710 to 714.

The singular forms "a," "an," and "the" refer to one or more than one, unless the context clearly dictates otherwise.

As used herein, the term "comprises" means "includes."

An "array" refers to a predetermined pattern, which can be either regular or irregular. Examples of arrays are linear distributions or two-dimensional matrices. As used herein, a group of individual members stated in the alternative includes embodiments relating to a single member of the group or combinations of multiple members. For example, the term "antibiotic, bronchodilator, or vitamin," includes embodiments relating to "antibiotic," "bronchodilator," "vitamin," "antibiotic and bronchodilator," "bronchodilator and vitamin," "antibiotic and vitamin," and "antibiotic, bronchodilator, and vitamin."

A "bioactive" composition, substance, or agent is a composition that affects a biological function of a subject to which it is administered. An example of a bioactive composition is a pharmaceutical substance, such as a drug or antibiotic, which is given to a subject to alter a physiological condition of the subject, such as a disease. Bioactive substances, compositions, and agents also include other biomolecules, such as proteins and nucleic acids, or liposomes and other carrier vehicles that contain bioactive substances. Bioactive compositions also may include pharmaceutical carriers, adjuvants, and salts.

"Drug" includes any bioactive composition administered for a therapeutic (including diagnostic) purpose.

"Mucosal" refers to the mucous membranes, the mucous-secreting membranes lining bodily passages open to the air, such as parts of the respiratory and digestive tracts. "Mucosal delivery" means application to a mucous membrane, including pulmonary or nasal inhalation.

Devices and methods are disclosed herein for improving the topical or inhalational application of drugs, or mucosal delivery of drugs, by using applicators based on inkjet technologies. Kits and systems for administrating drugs in this fashion also are described.

In some embodiments, an applicator is used to deliver a bioactive composition to a mucous membrane through a body orifice, such as a mouth or nose. The applicator includes a piezoelectric or thermal jet dispenser having a fluid ejection head with an orifice for ejection of droplets from the dispenser, with the jet dispenser at least partially enclosed within a main body. A fluid reservoir, for holding and delivering the bioactive composition to the orifice for ejection therethrough, is fluidically connected to the jet dispenser. In certain embodiments, the fluid reservoir is replaceable, such as a removable fluid reservoir that is at least partially insertable through the body of the jet dispenser. The applicator may include multiple fluid reservoirs containing the same or different compositions, including bioactive compositions, carriers, solvents, flavoring agents, and surfactants. A conduit fluid tubing system connects a fluid ejection head with a fluid reservoir. In embodiments having multiple fluid ejection heads and reservoirs, the conduit fluid tubing system may be a system of independent conduits with a separate conduit connecting each reservoir to a different fluid ejection head.

Some embodiments of the applicator also include a body orifice spacer positioned between the jet dispenser orifice and the target body orifice during ejection of the bioactive composition to the target. The spacer may be separate from or contiguous with the main body, such as a separate spacer mounted on an external surface of the body, and may be dimensioned in any appropriate manner, such as a tubular spacer sized for inhalation through the mouth or nose. In particular, non-limiting examples, the spacer is angled, or at least a portion of it extends transverse to the applicator body, to direct fluid transverse to the application body. For example, the fluids maybe delivered through the spacer at an angle of 30–120° to the central axis of the applicator body.

In specific embodiments, the applicator is an inhaler, such as a pulmonary or nasal inhaler. In alternative embodiments, a similar applicator is used for topical application of a bioactive composition to the surface of the subject, such as a patch of skin, rather than delivering the composition to a mucous membrane via a body orifice.

The droplets of bioactive composition delivered by the jet dispenser may be of a particular size. In some embodiments, the droplets are sized for respiratory inhalation or for delivery to bronchial airways. In other embodiments, the droplets are sized for delivery to nasal membranes or passages.

The applicator also may include a programmable controller, such as a microprocessor, for controlling the jet dispenser. The controller may be programmed via a keypad, touch screen, connection to a remote computer, removable memory device, or other suitable device.

Additionally, the applicator may be included as part of a kit for administering a bioactive composition to a subject.

The present disclosure concerns an applicator for inhalational or mucosal delivery of a bioactive composition using a jet dispenser, such as a piezoelectric or thermal jet dispenser. The dispenser includes a container or reservoir for holding the bioactive composition and delivering it to a fluid ejection head for ejection through a dispenser orifice, or an array of dispenser orifices contained on one or more ejection heads. The thermal or piezoelectric jet dispenser propels precise amounts of droplets from the dispenser toward a mucosal target. In some embodiments, such as the embodiment illustrated in FIGS. 1–3, a spacer also is provided between the dispenser orifice and a target body orifice (such as the mouth or nostril), to space the dispenser a desired distance away from the target body orifice during delivery of the bioactive agent. This spacer may be attached to the applicator, held in place in the orifice, or merely be interposed between them, to provide an interface across which the bioactive substance may be distributed from the dispenser orifice, or from the array of dispenser orifices, to a target body orifice. The target body orifice may be any natural or artificially created body orifice, such as an orifice created via surgery, such as via a tracheotomy.

In certain embodiments, the dispenser includes the bioactive agent in the reservoir. Examples of agents that can be included in the reservoir include pharmaceutical compositions that are capable of mucosal delivery. Such agents include drugs having sufficient permeability to move through a particular mucous membrane, such as a nasal membranes, intestinal epithelium, alveoli, and/or bronchial passages, into the bloodstream. Certain of these agents are designed to reach the microvasculature of the lungs for subsequent systemic absorption and distribution, or may be directed to a site of infection within the lungs. For example, an antibiotic composition may be designed to reach the lungs of a patient suffering pneumonia or other microbial infection of the lungs, while a psychogenic composition may be designed to be absorbed into the bloodstream through the lungs of a patient suffering some psychological disorder. Non-limiting examples of agents that are suitable for mucosal delivery include: bronchodilators, such as anticholinergic drugs, calcium antagonists, sympathomimetic drugs, corticosteroids, and xanthine drugs; antibiotics, such as natural and synthetic penicillin, cephalosporins, and aminoglycosides; analgesics, including natural semisynthetic, and synthetic opiates; antihistamines; psychogenic drugs, such as psychostimulants and psychopharmacologic agents; and vitamins and other nutritional supplements. Non-limiting examples of particular drugs may be found in *Remington: The Science and Practice of Pharmacy*, $19^{th}$ Edition (1995) on page 1583, for example in Chapter 56 (respiratory drugs).

Many analogues of these drugs retain their biological activity and are also suitable for mucosal delivery. Although the disclosed dispenser is particularly suited for mucosal delivery of drugs, it can also be used for topical surface application of certain bioactive compositions, such as antibiotics, corticosteroids, minoxidil or retinoids, (such as Retin A), by spraying a bioactive composition onto a patch of skin.

The reservoir holding the bioactive composition may be a fixed part of the applicator, for example, in a single-use, disposable applicator. However, in some embodiments, the reservoir is replaceable. In particular embodiments, one or more bioactive compositions are contained within multiple replaceable reservoirs. A replaceable reservoir allows greater flexibility in choosing particular drugs, or other bioactive compositions, for use with the applicator. For example, a series of replaceable reservoirs could contain a single drug in sequentially increasing or decreasing concentrations, or a series of different, but related, drugs for the treatment of a particular condition. Additionally, the use of replaceable reservoirs provides a more cost-effective alternative than fixed reservoirs, since only the empty reservoirs—and not the entire applicator—would need to be thrown away and replaced. In alternative embodiments, the replaceable reservoirs may be exchanged with minimal manipulation of the applicator. For example, as described in further detail below, the reservoirs of the embodiment illustrated in FIGS. 1–3 may be exchanged without breaking open the main body of the applicator. In such embodiments, exchanging or replacing the reservoirs may be less complicated than if the reservoirs were accessible only by opening the main body of the applicator. An easier to use applicator may enhance user adherence to a particular regimen and allow physicians greater flexibility in choosing and tailoring treatment regimens. Additionally, if the replaceable reservoirs are insertable through the main body of the applicator, mechanisms allowing easy access to the interior of the main body (e.g., a hinged opening) are not necessary, thus eliminating some manufacturing costs.

The dispenser also may include a controller for manually or automatically dispensing the bioactive substance from the dispenser at selected times. The controller may take the form of an actuator that is manually depressed to activate the dispenser and dispense the agent. Alternatively, the controller may be a programmable device, such as a microprocessor, that is programmed to dispense the bioactive agent at predetermined intervals, for example several times a day. In some embodiments, the controller includes a audible or visible cue, such as a tone or light, to alert the subject that a dose of the bioactive composition is ready to be dispensed. Alternatively, the controller may be used to adjust the dosage of an administered drug for a particular circumstance, such as a particular time of day, an event (such as an activity that will require a dosage modification), or detection of a physiological condition (such as an adverse drug reaction that requires reduction or cessation of drug administration). Complex administration protocols may be followed, for example applying different drugs at different times throughout the day or for longer periods, such as a week, a month, or even longer.

In certain embodiments, the container may carry multiple container modules, such as removable and replaceable modules that contain a bioactive agent. A container module may contain some other composition, such as a carrier, surfactant, solvent, or flavoring agent. Several modules may contain the same or different bioactive compositions, or some other composition, for example different compositions that combine before or at the time of delivery to modify one or both of the agents, or to produce a desired bioactive effect.

An example of a modifying substance that may be combined at the point of ejection is a penetration enhancer that improves mucosal penetration of the other bioactive substance. Penetration enhancers that may be mixed with a bioactive agent at the time of delivery include solvents such as water; alcohols (such as methanol, ethanol and 2-propanol); alkyl methyl sulfoxides (such as dimethyl sulfoxide, decylmethyl sulfoxide and tetradecylmethyl sulfoxide); pyrrolidones (such as 2-pyrrolidone, N-methyl-2-pyrroloidone and N-(2-hydroxyethyl)pyrrolidone); laurocapram; and miscellaneous solvents such as acetone, dimethyl acetamide, dimethyl formamide, and tetrahyrdofurfuryl alcohol. Other penetration enhancers include amphiphiles such as L-amino acids, anionic surfactants, cationic surfactants, amphoteric surfactants, nonionic surfactants, fatty acids, and alcohols. Additional penetration enhancers are disclosed in *Remington: The Science and Practice of Pharmacy,* 19th Edition (1995) on page 1583. Of course agents such as penetration enhancers also may be premixed with the bioactive agent prior to the point of ejection, for example the bioactive agent and modifying substance can be mixed together in the container.

The bioactive agent may be any flowable fluid (for example a liquid, gel or powder), although liquids are used in particular embodiments of the dispenser. In some embodiments, at least one of the reservoirs contains a bioactive agent in powder or other dry form, such as ipratropium bromide powder. The powder or other agent is dispensed from the container, and may in some instances be combined with a liquid (such as a penetration enhancer, or solvent) en route to the target body orifice or mucosal delivery site. The interface provided by a spacer between the dispenser orifice and the target body orifice allows chemical reactions to occur, as well as phase changes to stabilize (such as a change from a solid to a liquid state). This interface also may provide flexibility in the distribution of the drug across a larger target area or volume, as compared to application of the agent from a dispenser orifice that abuts the target body orifice. The spacer can also provide a flow pathway, external to the main body of the applicator, in which the droplets can be entrained in respiratory flow during inhalation.

Using existing inkjet technology, distribution of the drug to the target may be carefully controlled and exact dosing of the drug may be achieved. Controllers may be used to dispense simple or complex drug regimens, which is of particular advantage in patients who require numerous daily medications. Computerized control of medication dosing, which may be programmed by medical personnel for subsequent automated delivery, can help avoid toxic drug interactions, overdoses, and deaths.

The applicator is suitable for use in a variety of ways. For example, the applicator may be intermittently used to introduce an agent into a target body orifice, such as the mouth, for administration of the bioactive agent. Alternatively, the applicator may be used to apply the agent to an area of skin for topical application of a bioactive composition, or used to transdermally introduce the bioactive agent.

In another embodiment, the applicator may be selectively retained in prolonged contact with the target body orifice, for example by securing the applicator to the subject's body with an attachment member, such as a strap or adhesive. In this manner, the active agent may be administered from the dispenser for a prolonged period of time. For example, the applicator may be included as a part of a mask or respirator, which may be of particular use in a hospital setting. A replaceable reservoir may be removed from the applicator and replaced to avoid the necessity of removing the applicator from the patient.

One particular embodiment of the device includes a piezoelectric or thermal jet dispenser that includes a plurality of removable modules in fluid communication with one or more dispenser orifices (such as an array of orifices) ejecting and directing a fluid from the dispenser orifices toward a target body orifice. A spacer may be carried by the dispenser and positioned to be disposed against the target body orifice while the dispenser ejects the pharmaceutical fluid from the dispenser. A programmable microprocessor in the dispenser may control ejection of the fluid from the dispenser orifice at pre-selected intervals, such as once or twice a day, every one to eight hours, or even every few minutes or seconds, or ejection can be triggered by a manual actuator, a sensor, or a feedback mechanism. In some particular embodiments, the applicator includes a sensor that detects a pressure drop in the spacer during inhalation. The sensor then triggers the controller to release a dose of the bioactive composition without further action by the subject. In this manner, a subject may trigger a dose of a bioactive composition simply by positioning the spacer against the mouth or nose and inhaling. In some embodiments an air intake vent is provided in the space to facilitate circulation of air through the spacer. Thus, the composition may be ejected by the dispenser orifice and dispersed into an airstream.

The pressure sensor also may be used to monitor the amount of composition released by the device during inhalation. For example, the sensor may measure the difference in pressure and duration of the pressure drop, and the controller (such as a microprocessor) may use this information to calculate an amount of composition released by the device. The controller may stop the release of the composition from the dispenser orifice prior the end of inhalation by the subject, if a sufficient amount of the composition has been released, or if the amount of composition released during inhalation is less than the programmed dosage, the controller may cause the device to emit a signal indicating that the subject should inhale another dose of the composition.

The device may further include a programming module, such as a keypad or touch screen for entering dosage information, a display screen for showing what information has been entered, and indicators (such as one or more lights or a display screen on the exterior of the device) that provide information about how much drug remains in the device. Display screens and touch screens also may provide information about medications in the device, and provide an interface through which other information about the medications or their administration can be entered and/or obtained.

The dispensers disclosed herein may be similar to liquid dispensers known as inkjet printheads used in inkjet printing mechanisms, such as printers, plotters, facsimile machines and the like, some of which are described, for example, in Durbeck and Sherr, *Output Hardcopy Devices,* Academic Press Inc., 1987 (ISBN 0-12-225040-0), particularly in chapter 13, pages 311–370. These technologies have in common the extraction of a small quantities of a fluid from a reservoir that is converted into fine droplets and transported through the air to a target medium by appropriate application of physical forces. This technology has been implemented in a variety of ways, but one of the common approaches has been thermal inkjet technology, in which liquids are heated using resistors to form drops and propel them from a chamber through an orifice toward a target. Another approach is piezoelectric inkjet technology, in which movement of a piezoelectric transducer changes a chamber volume to generate the drop.

A typical jet printing mechanism uses cartridges (often called "pens") which shoot drops of liquid colorant (generally referred to as "ink") onto a page. Each cartridge is a printhead formed with very small nozzles through which the ink drops are fired. Most often, the printhead is held in a carriage which slides back and forth along a guide rod in a reciprocating printhead system, with a target or print media, such as paper, being advanced in steps between each pass of the printhead. To print an image on media, the printhead is scanned back and forth across the page, shooting drops of ink in a desired pattern as it moves. Other printing systems known as "page-wide array" printers, extend the printhead across the entire page in a stationary location and print as the media advances under the printhead. The particular liquid ejection mechanism within either type of printhead may take on a variety of different forms, such as the piezoelectric or thermal printhead technology.

For example, two thermal ink ejection mechanisms are shown in U.S. Pat. Nos. 5,278,584 and 4,683,481, both assigned to the Hewlett-Packard Company and herein incorporated by reference. In a thermal system, a barrier layer containing fluid channels and vaporization chambers is located between a nozzle orifice plate and a substrate layer. The substrate layer typically contains linear arrays of heater elements, such as resistors, which are energized to heat ink within the vaporization chambers. Upon heating, an ink droplet is ejected from a nozzle associated with the energized resistor. By selectively energizing the resistors as the printhead moves across the page, the ink is expelled in a pattern on the print media to form a desired image (e.g., picture, chart, or text).

In piezoelectric inkjet technology, an activating pulse is applied to a piezoelectric plate or member attached to a plate, which then responds by flexing to propel an ink drop out of a nozzle. Several examples of piezo-electric inkjet printheads are described in U.S. Pat. Nos. 4,992,808; 6,186,619; and 6,149,968 (assigned to Xaar Technology Ltd.) and U.S. Pat. No. 6,193,343 and WO 00/16981 (assigned to Seiko Epson Corporation), herein incorporated by reference.

Some printhead designs use "snapper" reservoir systems, in which permanent or semi-permanent printheads are used in conjunction with a detachable reservoir carrying a fresh liquid supply, with the reservoir being snapped into place on the printhead. Another design uses permanent or semi-permanent printheads in what is known in the industry as an "off-axis" printer. In an off-axis system, the printheads carry only a small liquid supply reciprocally back and forth across the printzone, with this on-board supply being replenished through tubing that delivers liquid from an "off-axis main reservoir" placed at a remote, stationary location within or near the printhead. In both the snapper and off-axis systems, rather than purchasing an entire new cartridge which includes a costly new printhead, the consumer buys only a new supply of liquid for the main reservoir.

Figures 1, 2:
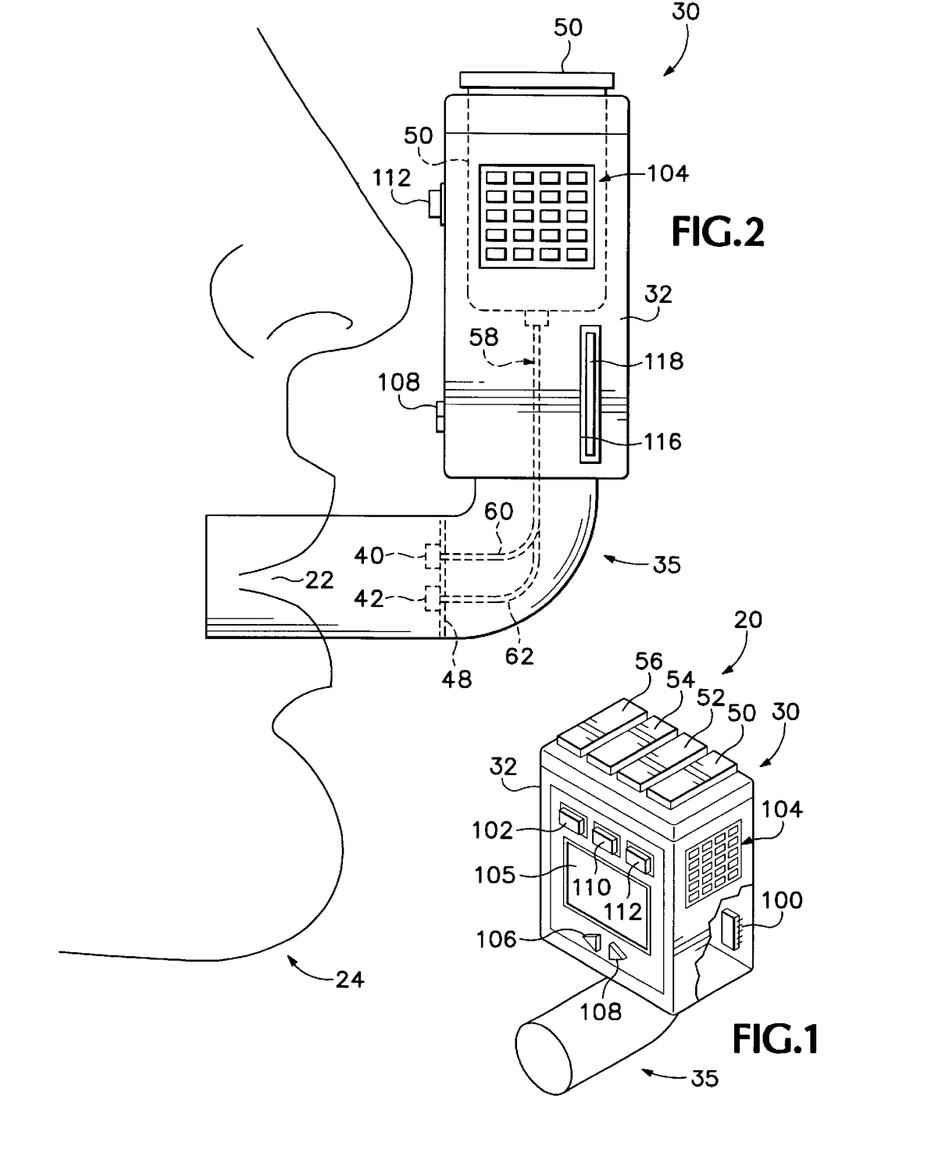
FIG. 1 is a perspective, fragmented, and partially schematic, view of one embodiment of the applicator having a tubular body orifice spacer.
FIG. 2 is an enlarged, side elevational view of the embodiment illustrated in FIG. 1, shown in place for use with a human subject as an oral inhaler.
Figure 3:
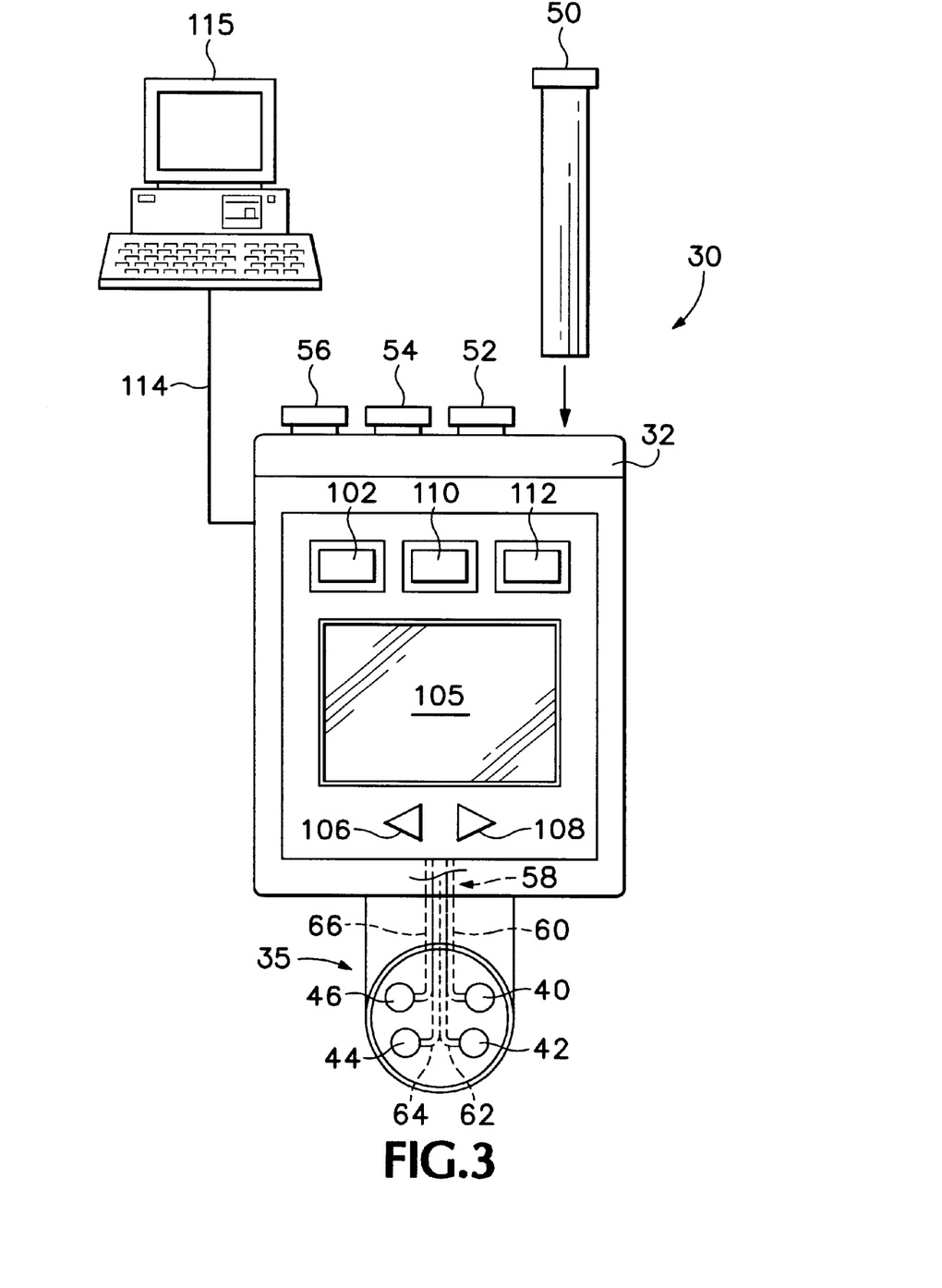
FIG. 3 is an enlarged, front elevational view of the embodiment of FIG. 1, showing a container module removed from the applicator and an array of four dispenser orifices arranged in the spacer. This figure also schematically illustrates the applicator connected to a remote control device, such as a computer.

In striving to duplicate the quality of photographic film images, the inkjet industry has focused on decreasing the size of ink droplets ejected from the nozzles, as well as accurately placing these droplets on the print media. For instance, some of the more recent inkjet print cartridges are able to deliver droplets about 3–6 picoliters in volume, although larger droplets also may be generated, for example droplets of 10, 50, 100, or more picoliters. The resolution within which currently commercially available inkjet printing mechanisms may place ink droplets on a page is on the order of 1200–2400 dots per inch (known in the industry as a "dpi" rating). Thus, while striving to achieve photographic print quality, inkjet printing technology has become very adept at accurately metering and dispensing fluids. This ability to dispense very small and accurate amounts of fluids (including liquids and powders) is a part of the application systems illustrated herein. For example, the jet dispenser may emit droplets sized for respiratory inhalation, for delivery to bronchial airways, or for delivery to other parts of the respiratory system, such as the throat or nasal passages. In particular embodiments, the droplets sizes are about 10 $\mu$m or less, such as about 2 $\mu$m to about 8 $\mu$m.

Additionally, differently sized droplets may be emitted for distribution for multiple parts of the respiratory system, such as distributing larger droplets throughout the bronchi and smaller droplets deeper into the lungs, such as to the bronchioles or the alveoli. These differently sized droplets may be of the same or different compositions (e.g., droplets of a first composition may be sized for distribution to the bronchi, while droplets of a second composition may be sized for delivery deeper into the lungs).

While these inkjet printheads may be used in the mucosal application systems illustrated here, rather than using a printing analogy, the printhead will instead be referred to in a more general nature as a "dispenser" or "dispenser head."

FIGS. 1–3 illustrate one particular embodiment of a mucosal or inhalational application system 20 for administering a bioactive composition to a subject, such as a pulmonary inhaler for the mouth 22 of a person 24. In alternative embodiments, the mucosal application system may be a different type of inhaler, such as a nasal inhaler, or a different type of applicator, such as a topical applicator.

The mucosal application system 20 illustrated in FIG. 1 includes applicator 30 (also referred to herein as a dispenser 30), which is illustrated as an applicator for dispensing a fluid (such as powder) chemical composition to a body orifice, such as a mouth 22. The applicator 30 includes main body 32 (also referred to herein as a body 32 and an applicator body 32), which may be coupled to body orifice spacer 35. While the illustrated applicator 30 includes a main body 32 that is separable from spacer 35, other embodiments may include a one-piece mamber defining both the body and spacer. In yet other embodiments, the system does not include a spacer.

The illustrated spacer 35 is tubular in shape, though spacers of different shapes may be used, such as rectangular, triangular, or other shapes. Additionally, while spacer 35 is illustrated for use with a human mouth, the body orifice spacer may be dimensioned for use with a different body orifice, such as a nasal opening (nares) or passage, or for a non-human subject. The spacer may be elongated along a longitudinal axis, and may be either straight, angled, or curved. For example, FIGS. 1-3 illustrates a curved tubular spacer having a fixed curved shoulder portion, which changes an air flor path in the spacer away from the spacer and toward the user. Thus, in this illustrated embodiment, the spacer extends substantially transverse to main body 32 and redirects the pathway of the bioactive composition from fluid reservoirs 50-56 to fluid ejection heads 40-46 via conduit fluid tubing system 58. Changing the delivery pathway of the fluid may be accomplished in another manner, however. For example, an alternative embodiment of the illustrated applicator may have the fluid ejection heads positioned at the base of main body 32 where spacer 35 is connected to body 32, rather than being positioned intermediately within spacer 35 by intermediate spacer wall 48. In such an alternative embodiment, the droplets of fluid are emitted by the fluid ejection heads in an ejection direction and, following the curved inhalation pathway, the spacer changes the direction of travel of these droplets from the ejection direction to a different delivery direction.

As shown in FIGS. 2 and 3, dispenser 30 is connected to one or more ejection heads, such as fluid ejection heads 40, 42, 44 and 46, by conduit fluid tubing system 58. The ejection heads are held in place within spacer 35 by intermediate spacer wall 48, and each ejection head contains at least one orifice for ejection of droplets of the bioactive composition from the dispenser. Ejection heads 40–46 may be constructed according to principles in the thermal inkjet technology, using piezoelectric ejection techniques, or other manners of fluid ejection. Indeed, the ejection of some chemicals may be benefited by a thermal ink ejection technology, in which elevated temperature can activate the agent. In contrast, other agents may chemically degrade and lose some or all bioactivity when heated in a thermal system, and such compositions may be dispensed using a piezoelectric or other non-thermal ejecting head technology.

The spacer 35 maintains a spacing between the ejection heads 40–46 and the subject, such as a spacing of greater than about 30 mil ($30 \times 10^{-3}$ inch), for example 1–3 mm, 3–10 mm, 1–5 cm, or a greater distance. This spacing permits a smooth, even dispersal of droplets within spacer 35 after ejection and before the bioactive composition contacts the subject. Additionally, this spacing protects ejection heads 40–46 from unnecessarily coming into contact with the subject's body, thus avoiding accidental damage to the ejection heads 40–46, or contamination of ejection heads 40–46 by dirt, debris, oils, saliva, mucous, or other substances carried by the subject. Such substances on the ejection heads 40–46 could potentially damage the ejection head nozzles, leading to fully or partially blocked nozzles that dispense less fluid than intended. Adequate spacing between the nozzles and subject's body also avoids capillary wicking of drug from the nozzles, which can lead to inadvertent or unwanted administration of the composition to the subject. Spacer 35 also may include a sensor or feedback mechanism (not shown), such as a pressure or temperature sensor, which may be used by applicator 30 in a closed-loop system, as described further below.

An angled spacer induces a particular delivery direction in relation to the applicator, thus allowing the applicator to be oriented for a particular use. For example, in the embodiment illustrated in FIGS. 1–3, angled spacer 35 is dimensioned for a human mouth 22, and the horizontal delivery direction created by the angled spacer allows the user 24 to observe the screen 105 while inhaling the bioactive agent. Additionally, the angled spacer may allow the flow of the agent to depend on or be assisted by gravity. For example, in the illustrated embodiment, the angled spacer 35 allows gravity-assisted vertical flow of the bioactive agent from the reservoirs 50–56 to the fluid ejection heads 40–46 through conduit fluid tubing system 58 while still allowing delivery of the agent from the fluid ejection heads 40–46 in a horizontal direction.

The fluid dispensed by ejection heads 40–46 may be stored in replaceable fluid reservoirs 50, 52, 54 and 56, respectively. As shown in FIGS. 2 and 3, the reservoirs 50–56 may be inserted into receptacles formed within main body 32 accessible from the outside of the applicator 30. Thus, reservoirs 50–56 may be removed from applicator 30 when empty and new reservoirs 50–56 inserted into applicator 30 without breaking open main body 32.

Following insertion of the reservoirs 50–56 into the main body 32, a conduit fluid tubing system 58 delivers fluid from the reservoirs 50–56 to fluid ejection heads 40–46 in spacer 35. As shown in FIG. 3, this conduit system 58 may include discrete fluid conduits, with each conduit independently connecting an individual replaceable fluid reservoir to an individual fluid ejection head. In the illustrated embodiment, the conduits 60, 62, 64 and 66 deliver fluid from the respective reservoirs 50, 52, 54 and 56 to their respective associated ejection heads 40, 42, 44 and 46. For example, replaceable fluid reservoir 50 is in fluid connection with fluid ejection head 40 via conduit 60, and replaceable fluid reservoir 56 is in fluid connection with fluid ejection head 46 via conduit 66. In alternative embodiments, the conduit fluid tubing system may be made of a single contiguous conduit system, or may be a multi-conduit system where two or more conduits have contiguous flow. The conduit system may be made from tubing running through the applicator, or conduits may be molded, bored or otherwise formed within the applicator.

To maintain ejection heads 40–46 relatively moist and free of clogs during periods of applicator inactivity, the application system 20 may include a protective ejection head storage and/or servicing member (not shown). For example, the head storage member may be a cap for the end of spacer 35 containing four ejection head protective members, such as elastomeric or foam printhead caps, positioned to seal ejection heads 40–46. Additionally, the head storage member (not shown) also may include one or more ejection head wipers, such as elastomeric wipers.

As illustrated in FIG. 1, applicator 30 includes an onboard ejection head controller 100, illustrated schematically for convenience. Controller 100 and ejection heads 40–46 receive power either from an onboard battery storage system (not shown) located in either main body 32, spacer, 35, or both. Alternatively, power may be supplied from an external source, such as a standard electrical outlet. Rechargeable or replaceable batteries may be employed in some embodiments for ease of portability and use. Controller 100 operates to apply firing signals to the ejection heads 40–46, which respond by ejecting fluid from reservoirs 50–56. In some embodiments, applicator 30 may include an ON/OFF power switch 102, to which controller 100 responds by beginning or ending a fluid ejection sequence. Alternatively, switch 102 may simply serve as an ON switch, with controller 100 determining the precise amount of fluid to be ejected from heads 40–46, and then stopping ejection automatically after the selected metered amount has been dispensed.

Multiple compositions can be dispensed simultaneously or sequentially. For example a different bioactive agent may be present in each of reservoirs 50–56 (e.g., a β-agonist, such as albuterol, in reservoir 50, a corticosteroid in reservoir 52, an anti-cholinergic drug, such as atropine or ipratropium bromide, in reservoir 54, and a mast cell stabilizer, such as cromolyn sodium, in reservoir 56), or a bioactive agent may be present in reservoir 50, while reservoirs 52–56 contain a solvent, surfactant, carrier, or flavoring agent. The multiple reservoirs provide the flexibility for the application to be programmed to respond to changing clinical circumstances. For example, only the corticosteroid from reservoir 52 would be administered to a subject having stable reactive airway disease. However, if symptoms persist, then the β-agonist from reservoir 50 also can be delivered (for example, in response to pressing an activation button or programming the applicator, for example, from a computer). If the disease progresses or becomes more severe, one or more of the bioactive agents from the reservoirs 54, 56 can be delivered from dispenser 30. The multiple bioactive agents may be administered sequentially or simultaneously. The user can be alerted to dispense the medication by an electronic signaler carried by dispenser 30, which emits an audible, tactile, or visible signal (such as flashing screen 105) when it is time for the medication to be dispensed. Alternatively, a dosage regimen can be altered by pre-programming the unit to respond to clinical information provided by the user (such as the answer to questions which the user enters into a computer) or in response to measurement of clinical parameters (such as blood oxygenation received by a portable pulse oximeter worn by the subject).

In alternative embodiments, applicator 30 may include an input keypad 104, such as an alpha or alphanumeric keypad. Using keypad 104, a physician, nurse, pharmacist, or other health professional, or the subject 24 to which the fluid will be administered, may input variations in the amount of and types of fluids dispensed by fluid ejection heads 40–46. Applicator 30 also may include a display screen, such as liquid crystal display 105, to indicate which selections have been made using keypad 104. Alternatively, keypad 104 may be eliminated, and the controller 100 programmed to display various selections on screen 105. Scrolling buttons 106 and 108 may allow different instructions or selections to be scrolled across, or up and down along, screen 105, including information such as desired dosages, frequency, and potential side effects.

In still other alternative embodiments, the display screen 105 also is a touch screen, in addition to, or in place of, keypad 104. The touch screen may include a series of images that, when touched with a finger or stylus, program the controller 100. Alternatively, the touch screen may include a character recognition area for receiving written inputs using a stylus, such as the graffiti recognition features of the Palm® operating system (Palm, Inc., Santa Clara, Calif.). Thus, a touch screen provides an alternative means for programming the controller in addition to the keypad.

Display screen 105 also may indicate various selections along an upper portion of the screen, adjacent buttons 102, 110 and/or 112, allowing a user to then select a particular drug or dosage by depressing one or more of these buttons. Alternatively, depressing one of the buttons could indicate the occurrence of a particular event, such as an adverse medication response that would alter (for example decrease) a subsequent dosage administration, or an event (such as physical exertion) than can signal a need to alter a medication dosage. The controller also may be programmed to prevent unauthorized alteration of dosages, for example an increase in a dosage of a controlled substance above that authorized by the prescribing physician. Alternatively, the controller can permit certain ranges of dosages to be administered, for example various doses of an opioid pain reliever in response to fluctuating pain.

As shown in FIG. 3, a more expedient method of initially programming controller 100, or supplying dosage and other information, may be to use a computer input conductor 114, selectively attachable to a receptacle on main body 32, to couple an external computer, microcomputer, or other input device 115 to controller 100. Other linkage devices may be used to communicate between external computing device 115 and controller 100, such as by using infrared signals, radio waves, modems, direct connections, and the like. For example, a patient can download information stored in the device about self-regulated dosage administrations or symptoms experienced (as indicated for example by which buttons have been depressed on the device, and/or the pattern and frequency of the buttons that are pushed). This information can be transmitted over a modem to a physician's or other health care provider's office, where it can be displayed (in electronic or other form) to a health care professional, and appropriate action can be taken. For example, if symptoms are noted to be increasing in spite of administration of a therapeutic amount of a particular drug, consideration can be given to providing a new drug or reconsidering the diagnosis for which the drug has been administered. As another example, the applicator may include a docking connection for use with a docking station connected to a computer at the physician's office. Thus, connecting the applicator to an external computer provides an alternative means for programming the applicator controller, in addition to the keypad and touch screen mentioned above.

The device also may be linked to communicate with multiple devices, such as devices for monitoring the physiological status of a subject. For example, the device may be linked to a blood sugar monitor and programmed to release an anti-diabetic drug if the subject's blood sugar level falls outside the normal range. As another example, the device may be linked to a temperature monitor and programmed to release a fever-reducing drug if the subject's body temperature rises above a certain threshold. The device may be programmed to automatically release a composition, such as in the case where the device is part of a respiratory mask worn by a bed-ridden patient, or may be programmed to signal the user that a dose of a composition should be administered to the user.

Alternatively, as shown in FIG. 2, main body 32 may define an input slot 116 which is sized to receive an input device, such as a flash memory card 118 or other removable memory device, which carries input data for controller 100. This removable memory device may be programmed by the applicator or some external device, such as a remote computer. For example, the removable memory may be inserted into and programmed by a computer at a physician's office, hospital, clinic, or other health facility and given to the subject for use with the applicator. Indeed, use of the flash memory card 118 or similar memory device in conjunction with controller 100, may result in the only other input device of applicator 30 being the ON/OFF switch 102. Alternatively, the switch may only be an ON switch, with the controller 100 ceasing fluid administration after a selected dosage has been administered. Thus, programmable removable memory provides yet another alternative means for programming the applicator controller, in addition to the keypad, touch screen, and remote computer connection described above.

In one embodiment applicator 30 may only have an ON switch 102, and be completely preprogrammed via an external computer 115, such as at a doctor's office or pharmacy, prior to giving the applicator 30 to a patient. In another embodiment, the applicator 30 may be sold with only an ON switch 102, and with the physician or pharmacy supplying one or more of the fluid reservoirs 50–56 in a kit with a flash memory card 118. In such an example, the kit includes one or more reservoirs 50–56 and a flash memory card 118. Alternatively, any combination of the components may be provided in the kit.

While each of the fluid reservoirs 50–56 may carry different bioactive agents, it also may be convenient to have each reservoir carry the same agent, with controller 100 applying fluid from first reservoir 50 until empty, followed by fluid from a second reservoir 52, and so forth. In such an embodiment, the applicator 30 may be programmed to indicate to the person 24, or an attendant, when fluid is being dispensed from the last reservoir, such as reservoir 56. This indication may take the form of displaying a message on screen 105, or simply by having an indicator light or a series of indicator lights mounted on the main body 32. For example, switch 102 may be back lit to turn a red color when the supply of active agent in the containers 50–56 is low.

As mentioned above, the applicator and/or spacer may include one or more sensors. For example, an optical sensor mounted inside the spacer may be used to determine whether the spacer is in position against a body orifice, such as a person's mouth. As another example, a pressure sensor may be mounted inside the spacer and used to detect a drop in pressure within the spacer, such as during inhalation. These sensors may be connected to the display, to the controller, and/or other parts of the applicator. For example, the optical sensor may be connected to a display to indicate to the user when the end of the spacer is firmly seated within the user's mouth. As another example, the pressure sensor may be connected to the controller and operate as an ON/OFF switch, triggering release of the bioactive composition from a fluid ejection head during inhalation (i.e., a drop in pressure) and stopping release when pressure is restored (i.e., when inhalation ceases).

Although certain examples on the dispenser have been disclosed for inhalational and/or mucosal administration of bioactive agents for the treatment of pulmonary disorders such as reactive airway disease, the dispenser is not limited to treatment of such disorders. Many bioactive agents can be delivered to the mucosal surfaces of the respiratory system for subsequent systematic action. For example, vasopressin may be administered intranasally in the treatment of central diabetes insipidus, and opiods (such as morphine) or benzodiazeprins (such as lorazepam) can be delivered by pulmonary inhalation, for example, in the relief of anxiety in lung cancer patients.

This specification has described several detailed examples, which are not intended to be limiting. Rather, these examples are provided to illustrate some of the embodiments which come within the scope of the following claims.

I claim:

1. An applicator for delivering a bioactive composition, comprising:

an inkjet dispenser comprising an orifice for high-speed ejection of droplets from the dispenser, the inkjet dispenser further comprising a main body;

a replaceable fluid reservoir for holding and delivering the bioactive composition to the orifice for ejection therethrough, the replaceable fluid reservoir at least partially insertable through the body; and a body orifice spacer positioned between the dispenser orifice and a target during ejection of the bioactive composition to the target;

wherein the dispenser comprises a first orifice and a second orifice, the first orifice operable to dispense droplets of a predetermined size, the second orifice operable to dispense droplets of a predetermined size different than the size of droplets dispensed from the first orifice.

2. The applicator according to claim 1 wherein the applicator is an inhaler.

3. The applicator according to claim 2 wherein the applicator is a pulmonary inhaler.

4. The applicator according to claim 1 wherein the inkjet dispenser is a piezoelectric droplet inkjet dispenser.

5. The applicator according to claim 1 wherein the spacer is external to the body.

6. The applicator according to claim 1 wherein the droplets of the bioactive composition are sized for respiratory inhalation.

7. The applicator according to claim 1 wherein the droplets of the bioactive composition are sized for delivery to bronchial airways.

8. The applicator according to claim 1, further comprising multiple replaceable fluid reservoirs.

9. The applicator according to claim 8 wherein the reservoirs hold and deliver two or more different bioactive compositions.

10. The applicator according to claim 1 wherein the spacer is a mouthpiece spacer or a nasal spacer and the inkjet dispenser is disposed within the spacer.

11. The applicator according to claim 10 further comprising a fluid conduit extending between the fluid reservoir and the inkjet dispenser to deliver bioactive composition from the fluid reservoir to the inkjet dispenser, the fluid conduit extending at least partially through the spacer.

12. The applicator according to claim 1 wherein:

said fluid reservoir comprises a first reservoir and a second reservoir;

said spacer defines an internal pathway;

said inkjet dispenser comprises first and second fluid ejection heads positioned in the internal pathway, each fluid ejection head having a respective orifice through which droplets of the bioactive composition are dispensed; and the applicator further comprises a first fluid conduit and a second fluid conduit, the first fluid conduit extending between the first fluid reservoir and the first fluid ejection head, the second fluid conduit extending between the second fluid reservoir and the second fluid ejection head.

13. The applicator according to claim 1 wherein the spacer changes a delivery direction.

14. The applicator according to claim 1, further comprising a programmable controller for controlling the inkjet dispenser.

15. The applicator according to claim 14 wherein the programmable controller is a microprocessor operable to dispense a predetermined amount of bioactive composition from the inkjet dispenser.

16. The applicator according to claim 14 wherein the controller is programmable from a remote computer in communication with the controller.

17. The applicator according to claim 14 wherein the controller is programmable from a keypad or touch screen mounted on an external surface of the body and in communication with the controller.

18. An applicator for delivering a bioactive composition comprising:
   an inkjet type dispenser comprising plural fluid ejection heads, each ejection head further comprising a dispenser orifice;
   multiple containers for holding and delivering the bioactive composition to the orifices, each container operably coupled to each fluid ejection head by an independent conduit; and
   a body orifice spacer positioned between the fluid ejection heads and a target during ejection of the bioactive composition to the target;
   wherein the multiple containers comprise a first container for holding a first bioactive composition and a second container for holding a second bioactive composition, and the dispenser comprises a first fluid ejection head and a second fluit ejection head, each having at least one dispenser orifice, the first fluid ejection head being configured to dispense droplets of the first bioactive composition having a predetermined size, an the second fluid ejection head being configured to dispense droplets of the second bioactive composition having a predetermined size that is different than the size of the droplets of the first bioactive composition.

19. The applicator according to claim 18 wherein the applicator is an inhaler.

20. The applicator according to claim 18 wherein the dispenser is a piezoelectric droplet jet dispenser.

21. The applicator according to claim 18 wherein the spacer is a mouthpiece spacer or a nasal spacer.

22. The applicator according to claim 18 wherein the spacer is dimensioned for at least partial insertion into a nose or mouth of a human.

23. The applicator according to claim 18 wherein;
   the spacer defines a delivery pathway substantially transverse to the applicator and has an open end for positioning at the target;
   the dispenser orifices are disposed in the spacer; and
   each dispenser orifice is spaced the same distance from the open end of the spacer.

24. The applicator according to claim 18, further comprising a programmable controller for controlling the jet dispenser.

25. The applicator according to claim 24 wherein the programmable controller is a microprocessor.

26. The applicator of claim 24 wherein the controller is programmed to sequentially deliver different bioactive compositions from different containers.

27. The applicator of claim 24 wherein the controller is programmed to simultaneously deliver different bioactive compositions from different containers.

28. The applicator of claim 24 wherein the controller is programmed to deliver bioactive compositions from the applicator in response to clinical or physical information.

29. An applicator for delivering a bioactive composition to a mucous membrane, comprising:
   a main body;
   a jet dispenser comprising first and second orifices through which droplets of a bioactive composition of a predetermined size are ejected, the size of droplets ejected from the first orifice being different than the size of droplets ejected from the second orifice;
   a container for holding and delivering the bioactive composition to the orifices for ejection therethrough; and
   a spacer positioned between the dispenser orifice and the mucous membrane during ejection of the bioactive composition to the mucous membrane, wherein the spacer extends substantially transverse to the body.

30. The applicator according to claim 29 wherein the container is in constant fluid communication with the jet dispenser such that the bioactive composition is allowed to flow from the container to the jet dispenser under the influence of gravity.

* * * * *